(12) United States Patent
Casarini et al.

(10) Patent No.: US 7,687,237 B2
(45) Date of Patent: Mar. 30, 2010

(54) METHOD OF IDENTIFICATION AND QUANTIFICATION OF PROTEINS, ISOFORMS OF THE ANGIOTENSIN I CONVERTING ENZYME

(75) Inventors: Dulce Elena Casarini, São Paulo (BR); Odair Marson, São Paulo (BR); Frida Liane Plavnik, São Paulo (BR); José Eduardo Krieger, São Paulo (BR)

(73) Assignee: Universidade Federal de Sao Paulo - UNIFESP, Sao Paulo (BR)

( * ) Notice: Subject to any disclaimer, the term of this patent is extended or adjusted under 35 U.S.C. 154(b) by 325 days.

(21) Appl. No.: 10/540,193

(22) PCT Filed: Dec. 22, 2003

(86) PCT No.: PCT/BR03/00202

§ 371 (c)(1),
(2), (4) Date: Jun. 20, 2005

(87) PCT Pub. No.: WO2004/057020

PCT Pub. Date: Jul. 8, 2004

(65) Prior Publication Data

US 2006/0057739 A1      Mar. 16, 2006

(30) Foreign Application Priority Data

Dec. 20, 2002   (BR) .................................. 0206903

(51) Int. Cl.
*G01N 33/53*   (2006.01)

(52) U.S. Cl. .................. 435/7.1; 435/90.1; 435/90.2
(58) Field of Classification Search ............. 435/7.1, 435/7.2; 436/516, 518
See application file for complete search history.

(56) References Cited

U.S. PATENT DOCUMENTS

2003/0062475 A1* 4/2003 Karst et al. ................. 250/288
2005/0147600 A1* 7/2005 Acton et al. ............. 424/94.64

OTHER PUBLICATIONS

Casarini et al. (Intl. J. Biochem Cell Biology 2001 vol. 33, p. 75-85.*
Hattori, et al., "*Angiotensin I-Converting Enzyme Isofoarms (High and Low Molecular Weight) in Urine of Premature and Full-Term Infants*", Hypertension. 2000:35:1284-1290.

* cited by examiner

Primary Examiner—Jacob Cheu
(74) Attorney, Agent, or Firm—Ohlandt, Greeley, Ruggiero & Perle, LLP

(57) ABSTRACT

The present invention relates to a method of identification and quantification of proteins, isoforms of angiotensin I converting enzymes (ACE), 190-kDa, specially of 90kDa in tissues, cells and biological fluids, specially in urine, genetic marker and prognostic agent of hypertension and primary or secondary renal lesion and kit for using in the diagnosis, risk stratification and therapeutical decision in arterial hypertension. One the aims of the present invention is to check the potential of the 90 kDa isoform as a hypertension genetic marker isoform and as a prognostic for hypertension.

9 Claims, 5 Drawing Sheets

N-terminal sequence of the 90 kDa and 65 kDa isoforms of angiotensin I converting enzyme

|  | 2 | 5 | 10 | 15 |
|---|---|---|---|---|
| 90 ACE | Asp Pro X | Leu Gln Pro Gly Asn Phe Ser | X Asp Glu Ala Gly Ala Gln Leu Phe | |
| 65 ACE | Asp Pro Gly | Leu Gln Pro Gly Asn Phe Ser Ala Asp Glu | X Gly Ala Gln Leu Phe | |
| Somatic ACE | Asp Pro Gly | Leu Gln Pro Gly Asn Phe Ser Ala Asp Glu Ala Gly Ala Gln Leu Phe | | |
| Rat ACE | Asp Pro Gly | Leu Gln Pro Gly Asn Phe Ser Ala Asp Glu Ala Gly Ala Gln Leu Phe | | |
| Mouse ACE | Asp Pro Gly | Leu Gln Pro Gly Asn Phe Ser Pro Asp Glu Ala Gly Ala Gln Leu Phe | | |
| Bovine ACE | Asp Pro Ala | Leu Gln Pro Gly Asn Phe Pro Ala Asp Glu Ala Gly Ala Gln Ile Phe | | |

Fig. 2A

C-terminal sequence of the 90 kDa and 65 kDa isoforms of angiotensin I converting enzyme 65 kDa :                                    GYLVDQXRXGVFS Somatic:    GLLDRVTNDTESDINYLLKMALEKIAFLPFGYLVDQWRWGVFSGRTPPSRY
               440       450       460       470       480

The 65 kDa enzyme ends at number 481 aminoacid

90 kDa:                                    EVLGXPEYQXHPP

Somatic: VGLDALDAQPLLKYFQPVTQWLQEQNQQNGEVLGWPEYQWHPPLPDNYPE
            590       600       610       620       630

The 90 kDa enzyme ends at number 632 aminoacid

Fig. 2B

METHOD OF IDENTIFICATION AND QUANTIFICATION OF PROTEINS, ISOFORMS OF THE ANGIOTENSIN I CONVERTING ENZYME

CROSS REFERENCE TO RELATED APPLICATIONS

The present application is a national stage entry filed under 35 U.S.C. § 371 of International Application No. PCT/BR2003/000202 filed on Dec. 20, 2003, published in English, which claims priority to Brazilian Patent Application No; PI 0206903-2 filed on Dec. 20, 2000.

FIELD OF INVENTION

The present invention relates to a method of identification and quantification of proteins, isoforms of angiotensin I converting enzyme (ACE), specifically ACE of 190-kDa, specially of 90 kDa (genetic marker of hypertension) and of 65 kDa in tissues, cells and biological fluids, specially in urine, a molecular marker based on said proteins, use of mentioned molecular marker, analytical method for diagnosis, risk stratification, therapeutical decision in carriers of arterial hypertension and primary or secondary renal lesion and kit for using in the diagnosis.

BACKGROUND OF THE INVENTION

The existence of two systems of vasoactive polypeptides, a hypertensor and a hypotensor, in mammal organism is quite new. The fundamental bases for understanding the hypertensor system, renin-angiotensin system were established through papers of Houssay and Fasciolo (1937), Houssay and Taquini (1938), Braun-Menendez, Fasciolo, Leloir and Munoz (1939) and Kohlstaedt, Helmer and Page (1938). On the other hand, the hypotensor system, kallikrein-kinin system are based on Frey, Kraut and Werle papers, carried out in the 1930 decade (Frey, Kraut and Schultz, 1930; Kraut et al, 1930; Werle, 1936; Werle et al, 1937) as well as Rocha and Silva, Beraldo and Rosenfeld (1949) and Prado, Beraldo and Rocha e Silva (1950).

In the two systems the vasoactive peptide is released to its plasmatic protein precursor through limited proteolysis according to the following general scheme:

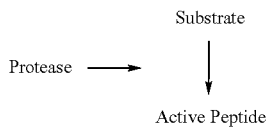

Several papers on purification and characterization of proteases and substrates involved in these two systems allowed the clarification of several steps necessary for releasing the active peptide. However, the physiological role of the latter, as well as its catabolism is not totally clarified yet.

The Renin-Angiotensin System

Renin is an acid protease (E.C. 3.4.99.19), produced and stored by juxtaglomerular cells from afferent arteriole of the renal glomerulus (Kohlstaedt et al, 1938; Hartroft, 1963 and Tobian, 1960). The subtract under which this enzyme acts is a plasmatic $\alpha_2$-globulin, angiotensinogen, from which part of the N-terminal sequence is known (Braun-Menendez et al, 1939; Bumpus et al, 1958; Schwyzer and Turrian, 1960) which corresponds to: $Asp^3$-$Arg^2$-$Val^3$ -$Tyr^4$-$Ile^5$-$His^6$-$Pro^7$-$Phe^8$-$His^9$-$Leu^{10}$-$Leu^{11}$ -$Val^{12}$-$Tyr^{13}$-$Ser^{14}$.

When renin hydrolisates the $Leu^{10}$-$Leu^{11}$ bond in the angiotensinogen molecule, decapeptide angiotensin I, which is as not very potent vasoconstrictor, is released. A second enzyme, described by Skeggs et al (1956), called converting enzyme, is the responsible by the hydrolysis of the $Phe^8$-$His^9$ bond and by releasing octapeptide angiotensin II, which is pharmacologically active, being inactivated by angiotensinases.

The Kallikrein-Kinin System

The kallikrein-kinin system comprises kininogenases which hydrolisates an inactive precursor, the kininogen, and releases kinins, which are inactivated by kininases.

The expression kininogenase comprises proteases, such as: kallikreins, trypsin, pepsin, some bacterian proteases and snake poison (Prado, 1970; Rocha e Silva et al, 1949; Suzuki and Iwanaga, 1970). Among these enzymes, kallikreins are specifics for the system: these are serine—proteases that release kinins of the kininogen, by limited proteolysis (Neurath, 1975) and have low proteolitic activity on other proteins. Two types of kallikreins are found in mammals: glandular and plasmatic, which are different each other concerning to physical-chemical and immunological proprieties, reaction velocity with kininogen and synthetic subtracts, types of kinins released and responds to a great variety of synthetic and natural inhibitors.

On the other hand, kininogens are acid glycoproteins which contains a bradykinin molecule in the C-terminal or next to it (Pierce, 1968); they are hydrolisated by glandular kallikreins, releasing lysyl-bradykinin, as well as by plasmatic releasing bradykinin (Rocha e Silva, 1974). Lysyl-bradykinin is converted to bradykinin by the existing aminopeptidases contained in plasma (Erdös and Yang, 1970) as well in tissues (Hopsu et al, 1966 a, b; Borges et al, 1974; Prado et al, 1975).

Two kininogens functionally different have been described in plasma, namely, a high molecular weight kininogen, which is subtract for the two kallikrein (plasmatic and glandular), and a low molecular weight, which is a good subtract only for glandular kallikrein (Werle and Trautschold, 1963; Prado et al, 1971).

Bradykinin (BK=$Arg^1$-$Pro^2$-$Pro^3$-$Gly^4$-$Phe^5$-$Ser^6$-$Pro^7$-$Phe^8$-$Arg^9$), lysyl-bradykinin and methionyl-lysyl-bradykinin are strong physio-pharmaco-pathological agents, which produces hypotension and vasodilation, pain, contraction of the smooth muscle, increases vascular permeability and leukocyte migration (Erdös and Yang, 1970; Pisano, 1975).

Physiological Role of Kinins:

The action of kinins in the organism is not totally clarified, although some attributions have been indicated them as participating in several physiological functions, either at systemic or tissular levels.

It is proposed its mediation in different processes such as: peripheric vasodilatation and mediation in inflammatory phenomena; interaction with the synthesis system and prostaglandins release; mobility of spermatozoids; renal flux regulation; mediation in the sodium reabsorption by nephron (Wilhelm, 1973; Terragno et al, 1975; Baumgarten et al, 1970; Schill and Haberland, 1974; Levinsky, 1979).

In order to clarify the exact role carried out by kinins in this process, it is important to know not only the mechanism that leads to its release but also to its catabolism.

Catabolism of Kinins:

The responsible enzymes for inactivation of kinins are generically known as kininases. Under this acronym it is comprised a series of peptidases which are capable to hydrolysate the bonds in BK molecule or its derivatives, not being necessary or prove to be participant of the kinins catabolism.

Observations on the existence of such class of enzymes have been carried out since the initial researches of the kinins system and have been described in several organs, tissues and physiological liquids by many researchers groups.

Plasma

Two types of kininases have been characterized already in the human plasma: kininase I (arginine carboxypeptidase, E.C. 3.4.12.7) and kininase II (peptidyl-dipeptidase, E.C. 3.4.15.1).

Kininase I is a carboxypeptidase type enzyme, which was purified for the first time from Cohn fraction IV (Erdös e Sloane, 1962). This enzyme hydrolysates the $Phe^8$-$Arg^9$ bonds of BK. It was originally called carboxypeptidase-N because of its proprieties, which make them different of pancreatic carboxypeptidase B. Although its official name, arginine carboxypeptidase, this enzyme catalyses better the lysine C-terminal hydrolysis than arginine, in many substrates (Oshima et al, 1975).

Among synthetic substrates used in the purification and specificity studies of such enzyme it can be cited the HLA (Oshima et al, 1975).

The second enzyme having kinin activity, described in plasma, is the kininase II, which inactivate BK by hydrolysis of the $Pro^7$-$Phe^8$ bonds and releases Phe-Arg dipeptides (Yang and Erdös, 1967).

Later, it was observed that such enzyme is identical to the angiotensin I converting enzyme (AI) of the renin-angiotensin system (Yang et al, 1970a and Yang et al, 1970b), therefore, being, responsible by hydrolysis of the $Phe^8$-$His^9$ bond of the AI molecule. One of the features of such enzyme is that it is inhibited by potentiator peptides of BK (BPP), described by Ferreira (1965), and Ferreira (1966).

It was also described in other animal species enzymes with similar specificity to those kininases I e II from human plasma (Erdös and Yang, 1970).

Lung

Great importance has been attributed to lung in which concerns BK elimination; many papers published by the literature describes the inactivation by this organ, regarding the high percentage of BK infused (Ferreira and Vane, 1967; Biron, 1968 and Dorer et al, 1974).

The kininase II has been already purified in hog lung (Dorer et al, 1972 and Nakajima et al, 1973) rabbit lung and rat lung (Soffer et al, 1974 and Lanzillo and Fanburg, 1974).

Studies of Ryan et al have contributed to clarify the mechanism of inactivation of this organ. BK would be inactivated, while AI would be converted into AII during the circulation, by an enzyme kininase II type that was in the pynocitotic vesicles of the vascular endothelium. Ryan et al, also observed that BK is much more easily hydrolyzed than LBK-BK and MLBK. Their theory is that these bigger kinins have a more difficult access to the vesicles. According to Ryan et al statement the BK hydrolysis products which were found after the lung circulation would be consequence not only from the action of the first cited enzyme but also from the action of other enzymes contained in the cytoplasm of endothelial cells (Ryan et al, 1968 and Ryan et al, 1975).

Liver:

Erdos and Yang attributed almost exclusively to the plasmatic and pulmonary kininases the responsibility for the kinin catabolism "in vivo". Researches carried out by Prado et al (1975) show, however, that other organs are able to inactivate kinins when they are perfused in weak rats, in which lung circulation was excluded from the perfusion circuit. In the referred paper when liver is perfused "in situ", it was shown that the organ inactivates considerable quantity of BK.

Following these researches, Borges et al (1976) observed that BK inactivation by the perfused liver "in situ" is due to, at least, two enzymes: a peptidyl dipeptide hydrolase and a second one that hydrolyzes the $Phe^5$-$Ser^6$ bond of BK. This enzyme could be a membrane peptidase, since it was removed from the perfused liver through the use of Triton X-100 in the perfusion liquid. According to the authors, the kinin activity obtained in this research is, very low when compared to those found in the supernatant of the total homogenate of the organ.

Mazzacoratti (1978) have worked with a preparation of this type, that is, homogenized liver from rats. It was purified two serine-proteases having different molecular weight which hydrolisates the $Phe^5$-$Ser^6$ bond of BK.

Brain

It has been studied by many researchers the metabolism of kinins in brain extracts (Iwata et al, 1969; Camargo et al, 1969).

Kininases from homogenized rabbit brain have been systematically studied by Camargo et al (1973), Oliveira et al (1976). Two thiol-endopeptidases optimum pH 7.5 were purified from the supernatant fraction. The first enzyme, kininase A, hydrolyzes the $Phe^5$-$Ser^6$ BK bond and has a molecular weight of 71 kDa; while the other, kininase B, hydrolysates $Pro^7$-$Phe^8$ as kininase II, but it has a molecular weight of 6900. This enzyme would be different from the converting enzyme (kininase II), since preliminary studies did not show the conversion of AI into AII.

Wilk, Pierce and Orlowiski (1979) described two enzymes from brain tissue which differs from the referred above. One of the enzymes, which was extracted from the bovine pituitary, also hydrolysates the $Phe^5$-$Ser^6$ Bk bond, however because of its molecular weight (higher than 100000) and because it is inhibited by $Na^+$ and $K^+$ it differs from kininase A. The second enzyme described, which was extracted from rabbit brain, is specifically for hydrolysis of those peptide bonds in which proline contributes with carboxyl group. This enzyme firstly hydrolyses the $Pro^7$-$Phe^8$ BK bond and secondly, the $Pro^3$-$Gly^4$ bond.

Kidney:

The kininase activity of kidney is higher than found in plasma or liver (Erdös and Yang, 1970).

Several enzymes have been purified, in this organ, with kininase activities. Researches of Erdos et al, have identified three different enzymes in the kidney: one, carboxypeptidase type, which releases arginine C-terminal of BK, which differs from some properties of plasmatic kininase I, this is why it was called kininase p (Erdös and Yang, 1966); another enzyme, which hydrolisates the $Pro^7$-$Phe^8$ bond (Erdös and Yang, 1967), and a third one, characterized as an imidopeptidase, which inactivates BK by hydrolysis of the $Arg^1$-$Pro^2$ bond (Erdös e Yang, 1966).

Koida and Walter (1976) purified, from sheep kidney, an enzyme that hydrolysates Pro-x bonds type in the molecule of several peptides, among which the BK. It was observed that the x aminoacid cannot be proline and that its catalysis is faster if x is a lipophilic aminoacid.

The kinin catabolism by the kidney has been studied by methods aiming at to identify the inactivation sites of such peptides. These studies indicate that, besides the BK hydrolysis that occurs at vascular network level, the catabolism of kinins by enzymes located at renal cortical cells seems to have great importance (Erdös and Yang, 1967).

The kininase activity is very low in the glomerulus, but a type II kininase is found in great concentration in brush border of the proximal convoluted tubule (Holl et al, 1976, Casarini et al, 1997). In agreement with this discovery, Oparil et al (1976) observed that a high percentage of BK microinfused is inactivated in the proximal tubule. Considering that the kinin generation in kidneys should occur close to the distal tubule, where kallikrein is synthesized (Ørstavik et al, 1976), it seems to be logical to suppose that from this point, other kininases should be present and the nephron or in the intratubular fluid.

Urine

A carboxypeptidase was well characterized by Erdös et al (1978), in human urine; it releases BK C-terminal arginine and differs from the plasmatic one as to molecular weight, inhibitors action and immunological proprieties. However, kinetic and inhibition similarities to renal enzyme are shown.

Ryan et al described, in 1978, three enzymes contained in urine: one enzyme hydrolyzates the $Pro^7$-$Phe^8$ BK bond and transform AI into AII; another enzyme, having 63 kDa molecular weight, which breaks the $Phe^8$-$Arg^9$ BK bond, is not inhibited by $BPP_{9a}$.

Figueiredo et al (1978) also described, a kininase having molecular weight of 250 kDa, which is inhibited by chelate agents that would be similar to the third among those described by Ryan. This enzyme hydrolysates C-terminal arginine, although it does nor hydrolysates the HLA synthetic substrate.

With the exception of Erdös et al, 1978, research that have purified and characterized a carboxypeptidase from urine, all researches, however, the described enzymes were only partially purified and/or characterized. Due to these contradictory data, the present invention aims at to characterize the different kininase activities that are the ACE in human urine.

One of the forms of low molecular weight (LMW) of the angiotensin I converting enzyme of 91 kDa was observed during the preparation of such enzyme from rat lung homogenate [Lanzillo et al, 1977]. This LMW form from ACE was also observed in human lung [Nishimura et al, 1978], hog kidney [Nagamatsu et al 1980] and human kidney [Takada et al, 1981]. Iwata et al (1983) and Yotsumoto et al (1983) have shown that ACE LMW of 86-90 kDa can be obtained from rabbit lung and human plasma, respectively, after treatment with bases. In the 90' Lantz et al (1991), described three different ACE isoforms having molecular weights of 150 kDa, 80 kDa and 40 kDa characterized in the human cerebrospinal fluid. All the previously referred are similar to somatics. Casarini et al, 1991, 1995, 2001, described the 65 kDa and 90 kDa isoforms, both N-domain in hypertense patients urine and 65 kDa on normal persons. Deddish et al (1994) purified an ECA with 108 kDa molecular weight in ileal fluid, which is also an N-domain isoform of ACE.

It has been described the purification of several isoforms of ACE [Ryan et al, 1978; Kokubo et al, 1978; Skidgel et al, 1987; Casarini et al, 1983, 1987]. Kokubo et al (1978) found three different forms of ACE normal human urine. Two forms with high molecular weight of >400 kDa and 290 kDa and a third one, molecular weight of 140 kDa. Ryan et al (1978) described a kininase II human urine that was separated in two forms. The first co-cromatography with somatic ACE of 170 kDa, and the second was similar to a protein having molecular weight of 90 kDa. Casarini et al (1983, 1991, 1992, 1995, 2001) described he ACE in human urine of normal persons and hypertense patients with molecular weights of 190 kDa, 90 kDa and 65 kDa and also in rat urine (Casarini et al 1987). Alves et al, 1992 also described isoforms of 170 kDa, 90 kDa and 65 kDa in urine of normal persons and hypertense patients. Costa et al, 1993, 2000 described in normal persons urine, ACE with different molecular weights of 170 kDa, 65 kDa and 59 kDa, and in the hypertense patients, renovasculares enzymes with molecular mass of 55 kDa, 57 kDa e 94 kDa. The ACE activity in urine is not from the plasma but from the renal tubule (Casarini et al, 1997) and can be used as a reference for the renal tubular damage, since there is a considerable level increasing in renal and infections of upper urinary treat diseases [Baggio et al, 1981; Kato et al, 1982].

It was also recently described, two ACE isoforms in intracellular and extracellular medium of mesangial cells in culture, having molecular weight of 130 kDa and 65 kDa (Andrade et al, 1998). It was still observed the presence of 190 kDa and 65 kDa isoforms in children urine but in premature children only 65 kDa isoforms ACE, being the latter similar to the N-domain portion of the same. In premature children, it was found, in a period of 1 to 30 days after they were born, that these 190 kDa isoform would appear only in the thirtieth day (Hattori et al, 2000).

BRIEF DESCRIPTION OF DRAWINGS

FIG. 1A: Normotensive children/normotensive parents (At 280 nm—ACE Activity on the HHL substrate).

FIG. 1B: Normotensive children/hypertensive parents (At 280 nm—ACE Activity on the HHL substrate).

FIG. 1C: Hypertensive children/hypertensive parents (At 280 nm—ACE Activity on the HHL substrate).

Urine of normotensive persons with hypertensive parents has presented the three ACE isoforms having 190 kDa, 90 kDa e 65 kDa molecular weights, showing that the 90 kDa premature isoform appears. Thus, showing to be a prognostic that these persons (individuals) could get hypertension, being, therefore, a genetic marker for hypertension.

FIGS. 2A and 2B: Presentation of N-terminal and C-terminal sequence of 90 kDa and 65 kDa angiotensin I isoforms converting enzymes. The 65 kDa enzyme ends at the number 481 aminoacid. The 90 kDa enzyme ends at number 632 aminoacid.

Figure 1:
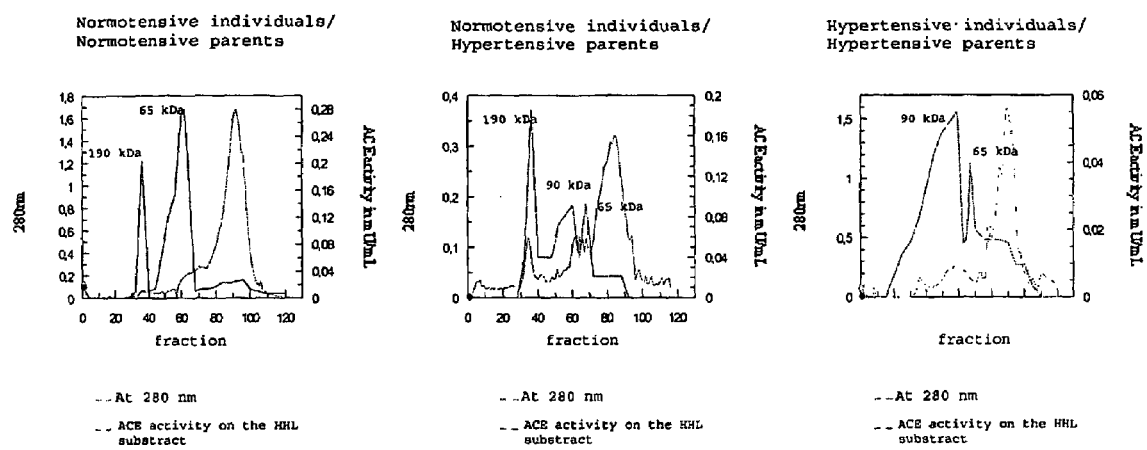
FIG. 1 (A, B, C): Shows a gel Chromatography filtration in Ac A-34 column of human urine.
Figure 3:
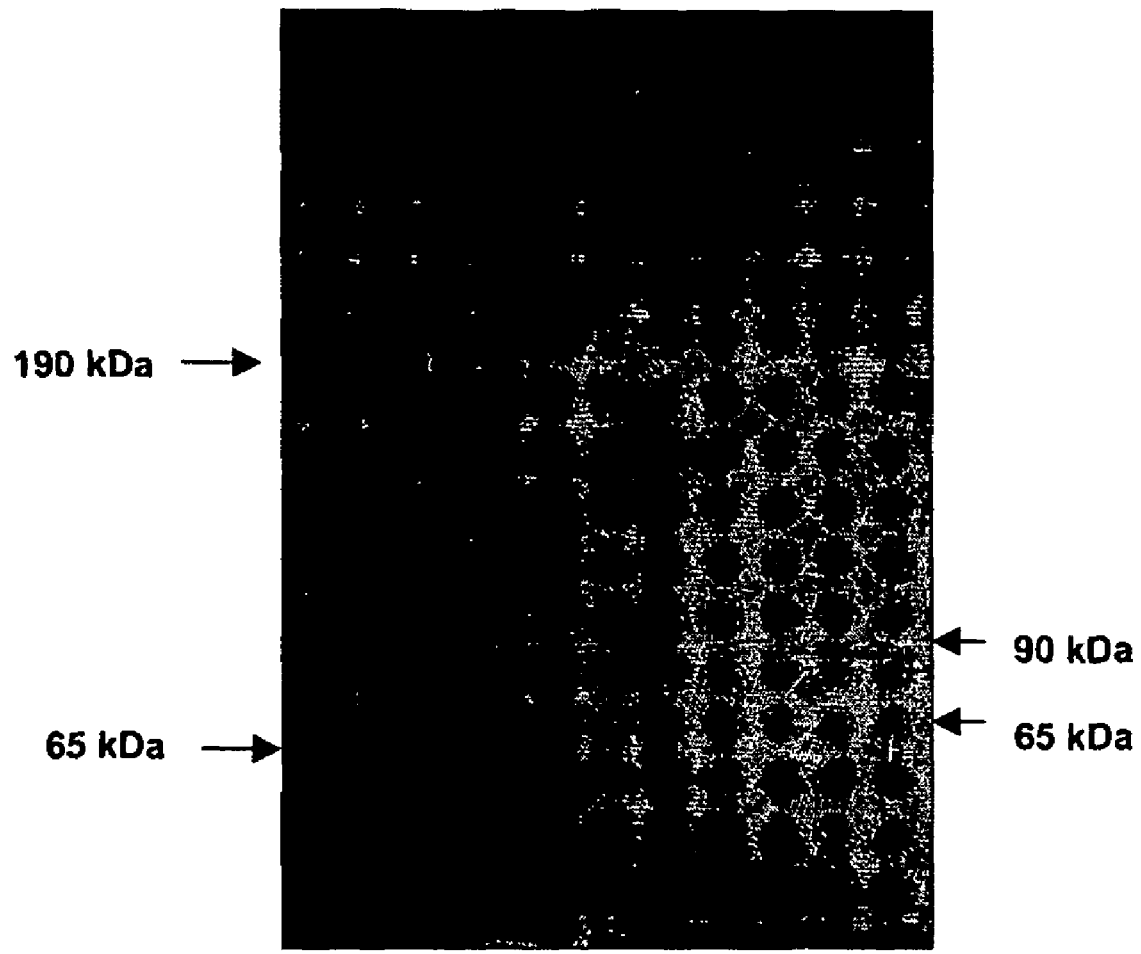

FIG. 3: Fresh human urine Western Blotting—Line 1: normal person urine, Line 2: wild ACE recombinant, Line 3: ACE recombinant secreted, Line 4: hypertensive patient urine.

Figure 4:
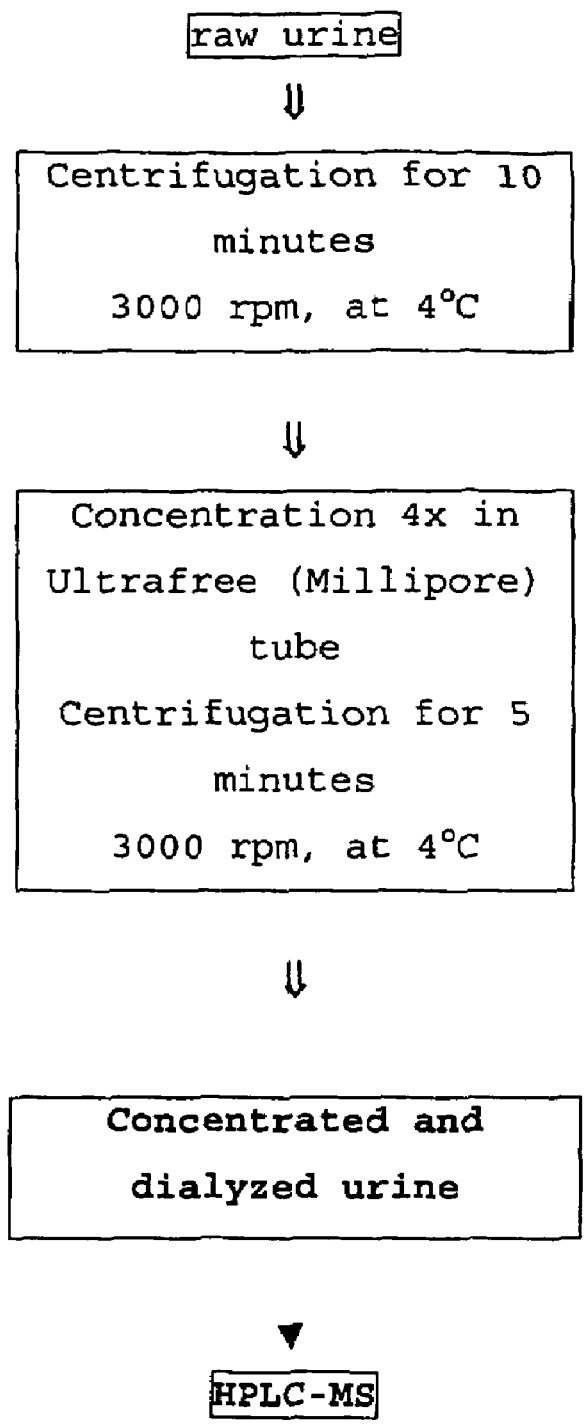

FIG. 4: Scheme of dosage by mass spectrometer—the scheme presents 5 (five) steps which starts by raw urine that in the second step is centrifuged for 10 minutes at 3000 rpm speed and at 4° C. temperature. In the third step, urine is concentrated 4× (four times) in a Ultrafree (Millipore) tube and is centrifuged during 5 (five) minutes at 3000 rpm and 4° C., then going to a forth step where concentrated urine pass through a dialysis in centricon Tris/HCL 1 mM buffer, pH 8.0 centrifuged during 5 (five) minutes at 3000 rpm and 4° C., resulting in a concentrated urine and dialyzed and finally, the fifth step which results the HPLC-MS.

DESCRIPTION OF THE INVENTION

In order to carry out the method of identification and quantification of proteins, isoforms of the angiotensin I converting enzyme, specifically 190-kDa ACEs, specially 90 kDa and 65 kDa in tissues, cells and biological fluids, specially in urine, according to the present invention, it starts with collecting fluids, such as urine, tissues or cells from living organisms, submit them to a chromatographic separation (AcA44 and/or AcA 34 resin; reverse phase column C-18, in mass spectrometer) and by Western Blotting (using a specific antibody against somatic ACE and N-domain ACE [90 kDa, genetic marker for hypertension and 65 kDa] of 190 kDa, 90 kDa and 65 kDa isoforms. Normal individuals have the 190 kDa and 65 kDa isoforms while the 90 kDa isoform (hypertension genetic marker) will characterize those individual predisposed to develop hypertension and lesion in characteristic target organs (heart, nervous system, vascular system and kidney).

The method of the present invention considers that an aliquot of fluid (for example, fresh or concentrated urine), cells and tissues are processed and analyzed by high performance liquid chromatography and detection by mass spectrometry (HPLC-MS) or directly in the mass detector, where the sample is analyzed and compared with the previously established standards for 190 kDa, 90 kDa (hypertension genetic marker) and 65 kDa ACE isoforms. An aliquot of fluid (for example, fresh or concentrated urine), cells and tissue are processed and analyzed by Western Blotting or another immunoprecipitation method) using specific antibodies against 190 kDa and N-domain ACE (90 kDa hypertension genetic marker and 65 kDa), using as a control analysis the ACE isoforms prepared as standards as well as the ECA recombinant enzyme.

In order to reach the results proposed by the present invention, the researches on ACE, started in 1983, when essential (light and/or mild forms) arterial hypertensive patients were analyzed after using captopril (50 to 150 mg) orally administered in one-day dose. Three days study, each day, each six hours collect duration; samples of blood and urine were collected at the final basal period (1 hour), after they reach the supine position, as well as at the end of the study (after 6 hours). The results show a 50% inhibition on the enzyme activity, in a period between 1 and 2 hours after captopril administration, returning to the basal levels at the end of the studies. The enzymatic activity using Hipuril-His-Leu substrate was measured by Friedland and Silverstein method (1976). Through ion exchange chromatography analysis, the collected urine (collected after 6 hour) two protein peaks were eluted with angiotensin I converting activity and inactivated for bradykinin, in conductivity of 0.7 mS (90 kDa) and 1.25 mS (65 kDa), differing from the profile found in 190 kDa e 65 kDa ACE in normotensive individuals. Based on this, studies have been developed with a higher number of light hypertensive patients, where it was found the presence of two protein peaks with angiotensin I converting activity, as cited above (Casarini et al, 1991).

Following the studies as referred above (project support by FAPESP, No 95/9168-1) the following study groups were organized: normal parents/normal children; normal parents/hypertensive children; hypertensive parents/hypertensive children and hypertensive parents/normal children. It was found that the group (normal parents/hypertensive children) hypertensive parents/hypertensive children, the children urine was presented two 90 e 65 kDa forms; in the normal parents/normal children group, the children urine presented the 190 and 65 kDa forms; and, finally, in the hypertensive parents/normal children, the children urine presented the 190, 90 and 65 kDa forms, being these two last forms, N-domain fragments.

From these results, it was concluded that 90 kDa would possibly be a hypertension marker. In order to prove if this findings was a genetic factor or another fact related or not to pressure increasing (physical), data were validated in the same project in the experimental model for rats. For this purpose, it was studied Wistar Brown Norway, Lyon, SHR, 1R1C and DOCA-salt rats urine. As a result, the Wistar, DOCA-salt, 1R1C and Brown Norway rats presented 170 and 65 kDa forms; only SHR and SHR-SP rats presented the 90 and 65 kDa forms. These results confirm those obtained for humans, thus, being, the 90 kDa ACE isoform a hypertensive genetic marker (Fapesp 97/00198-0, Marques 1999).

In 1997, researchers of the present invention described that the mesangial cells in a culture that expresses the ACE RNAm (Casarini et al, 1997). This enzyme is detected in the intracellular (136 kDa and 65 kDa) and secreted (136 kDa e 65 kDa), indicating a potential effect of the local production of angiotensin II in the function of these cells (Fapesp 95/9168-1; Andrade et al, 1998).

It was observed latter that the intracellular and the culture means of the SHR mesangial cells presented the same profile of (90 and 65 kDa) ACE isoforms, which were found in urine of such rats (Fapesp 99/01531-1); therefore, this confirms the results of the previous researches. From these results, it was observed by the authors of the present invention, that these isoforms are expressed in the lung, adrenal, heart, aorta and liver of Wistar rats (136 kDa and 69 kDa) and SHR (96 kDa and 69 kDa) and are not restricted to kidney (Ronchi, 2002); emphasizing that the 80/90/96 kDa hypertension genetic marker is expressed in the various tissues and, therefore, bringing to conclude that these isoforms can contribute for a regulation of the specific organ (it should be stressed that when de 80 or 96 or 90 kDa enzymes are referred, it should be understood, the same enzymes with small alteration in the glycolization process).

The present invention starts with fluid collect as for example urine, tissue or living organisms cells, that are submitted to a chromatographic separation (resin AcA44 and/or AcA 34; phase reverse column C-18, mass spectrometer) and by Western Blotting (using a specific antibody against ACE somatic and against ACE N-domain [90 kDa, hypertension genetic marker and 65 kDa] of 190 kDa, 90 kDa and 65 kDa isoforms. The 190 kDa and 65 kDa isoforms will be present normal individuals (normal rats, cells and/or tissue from normal rats); while the 90 kDa (hypertension genetic marker) isoform will characterize those (individuals or animals, etc) predisposed to develop hypertension and lesions in characteristics target organs (heart, nervous system, vascular system and kidney). A aliquot of fluid (for example, fresh or concentrated urine), cells and tissue are processed and analyzed by high performance liquid chromatography method and detection by using mass spectrometry (HPLC-MS) or directly in the mass detector, where the sample is compared with the standards established for ACE of isoforms 190 kDa, 90 kDa (hypertension genetic markers) and 65 kDa. An aliquot of fluid (for example, fresh or concentrated urine), cells and tissue are processed and analyzed by Western Blotting using specific antibodies against 190 kDa ACE and N-domain ACEs (90 kDa), hypertension genetic marker and 65 kDa), using as analysis control the ACE isoforms prepared as standards and the recombinant ACE enzyme.

Ace Isoform as Hypertension Marker

Isoform of Angiotensin I Converting Enzyme (90 kDa, N-Domain) as a Hypertension Genetic Marker Produced by Human Urine:

Based on the previous studies, the researchers of the present invention found in normotensive individuals urine and using ion exchange chromatography, two peaks of angiotensin I converting activity with molecular mass of 196 kDa and 65 kDa. When hypertension patients urine is processed, it was obtained a profile where two peaks were eluted with angiostensin I converting activity in the 90 kDa and of 65 kDa molecular weight, not being detected the 190 kDa form (Hypertension 26:1145-1148, 1995).

One of the objectives of the present invention consists in confirming the potential of the de 90 kDa isoform as a hypertension genetic marker and as a hypertension prognostic.

The following study groups were established for this purpose:

normotensive individuals with normotensive parents,
normotensive with hypertensive parents
hypertensive with normotensive parents, and
hypertensive with hypertensive parents.

The collected urines were concentrated separately and dialyzed with Tris-HCl 50 mM buffer, pH 8.0 and then submitted gel filtration in AcA-34 column equilibrated with Tris-HCl 50 mM buffer, containing NaCl 150 mM, pH 8.0. The collected fraction (2 mL) have been monitored by reading the absorbance in 280 nm and by the angiotensin I converting activity, using Hipuril-L-His-L-Leu- and Z-Phe-His-Leu as substrates. The following results was obtained: normotensive individuals with normotensive parents presented two isoforms with ACE activity (190 kDa and 65 kDa) (n=21); normotensive individuals with hypertensive parents presented three (190 kDa, 90 kDa and 65 kDa) (n=13) isoforms and hypertensive individuals with hypertensive parents presented two isoforms (90 kDa and 65 kDa) (n=13). As expected, it was not found anybody that would constitute the hypertensive group with normotensive parents.

Two individuals that presented 190 kDa, 90 kDa and 65 kDa isoforms, normal pressure, and that were in contact with the research group, were monitored for 4 years. In the forth year after detection of isoforms in the urine, they became hypertensive; this proves, therefore, that the 90 kDa isoform is really a hypertensive genetic marker.

Conclusion:

Considering that the urine of normotensive individuals with hypertensive parents presented the three ACE isoforms with molecular weight of 190 kDa, 90 kDa and 65 kDa, shows that the 90 kDa isoform which early appears, is a prognostic that these individuals could be a hypertensive person, thus, being, a hypertensive genetic marker.

Quantification and Identification of the Ace Isoform, Hypertension Genetic Marker by Mass Espectrometry and Western Blotting Western Blotting of the Human Fresh Urine:

Urine was collected from a single time in the presence of a "pool" (several inhibitors) of proteases, then, it was concentrated and 100 ug was submitted to a 7.5% polyacrylamide gel electrophoresis, followed by Western Blotting with PVDF membrane, then it was incubated with the polyclonal antibody Y1 against human ACE. Line 1: urine of normal individual, Line 2: ACE wild recombinant, Line 3: ACE recombinant secreted, Line 4: hypertensive individual urine.

Dosage for Mass Espectrometer:

Raw urine was centrifuged for 10 minutes, at 3000 rpm, 4° C., followed by 4× concentration in Ultrafree (Millipore) tube, then centrifuged for 5 minutes at 3000 rpm, 4° C., dialyzed with centricon Tris/HCl 1 mM buffer, pH 8.0. Then, it is centrifuged for 5 minutes, at 3000 rpm, 4° C. Concentrated and dialyzed urine was, then, obtained and therefore, the prepared sample was analyzed in HPLC-MS.

The solvents used in the HPLC system were: solvent A, which consists of 0.1% trifluoroacetic acid (TFA, Merck, Germany). The urines were separated in a Nova Pak $C^{18}$ (Waters) reverse phase column, for 15 minutes with a 1.5 mL/min flux. The conditions are still been standardized in order to improve the method resolution.

Isoform of Angiotensin I Converting Enzyme (90 kDa) as a Hypertenssive Genetic Marker Secreted in Rats Urine. Protocol Design to Prove the Findings (Affirmation of Genetic Marker for the 90 kDa Protein) with Human Urine.

ECA isoforms presented in isogenic normotensive rats (WKY and Brown Norway) urine have been identified as well as in normotensive, isogenic hypertensive (SHR, SHR-SP, Lyon), isogenic normotensive, experimentally hypertensive (1K1C and DOCA-Salt) and isogenic hypertensive rats, which were treated with antihypertensives drugs (SHR+enalapril), aiming at to compare the obtained chromatography profiles, and with the objective to characterize the 90 kDa form as an arterial hypertensive genetic marker.

From WKY rats urine, two peaks of AI converting activity have been separated by gel filtration in AcA-44 resin: the first, WK-1, corresponds to a high molecular enzyme (190 kDa) and the second one, WK-2, corresponds to a low molecular weight (65 kDa); these data were confirmed by Western Blotting. In the SRH group, the chromatographic profile have presented different results from the previous group (WK), being identified an ACE called S-1, with molecular weight 80 kDa, and a second one, S-2, molecular weight of 65 kDa, similar to those found in hypertensive patients urine that was not 90 kDa and 65 kDa treated (Casarini et al., 1991). The molecular mass differences between the 80 kDa enzyme from rat and the 90 kDa enzyme of human urine occur due to the glycolization process (data not shown).

In the third group (1K1C), a renovascular induced hypertension model, the chromatography profile was similar to the one found in rats used as control (WKY). In this group two peaks of AI converting activity were obtained: the first, C-1, corresponds to a 190 kDa enzyme and the second one, C-2, to 65 kDa.

Two peaks of AI converting activity were separated by gel filtration in AcA-44 resin, from SHR-SP rats urine: the first one, called SP-1, corresponds to a 80 kDa enzyme and a second one, called SP-2, which corresponds to the 65 kDa enzyme, similar to that found in SHR rats urine and also found in not-treated hypertensive patients urine (Casarini et al, 1991, 1995).

On the other hand, the SHR rats, which were treated with enalapril, show that although having their pressure under control, they carry the 80 kDa isoform; this fact shows that the isoform profile is linked to genetic factors.

In the group of rats used as control, the DOCA-Salt model, in which it was not administered the hypertensive treatment, the chromatographic profile was similar to that found for normotensive WK rats. Two peaks with AI converting activity were obtained: the first, CD-1, corresponds to a 190 kDa enzyme, and the second, CD-2, corresponds to the 65 kDa.

The DOCA-Salt model, with reduced hypertension induced by DOCA and saline administration, presented a chromatographic profile similar to that found in DOCA-Salt and WK control rats. Two peaks of AI converting activity were obtained: the first one, D-1, corresponds to 190 kDa ECA, and the second one, D-2, to 65 kDa ECA. This result shows that the 80 kDa presence is linked to a genetic factor not being consequence of the increasing of pressure.

The result of the gel filtration in Brown Norway normotensive rats urine was similar to the profiles found in normotensive rats urine. Two peaks with ACE activity have been obtained: BN-1, which corresponds to the 190 kDa enzyme, and the second one, BN-2, which corresponds to the 65 kDa enzyme, showing that different strain of normotensive presents the same chromatographic profile.

Comparing the chromatographic profiles of WK rats (normal control) urine, 1K1C (experimental hypertensive—Goldblatt), DOCA-Salt (control), DOCA-Salt (experimental hypertensive) and normotensive Brown Norway with the urine of SHR rats, Lyon and SHR-SP (genetically hypertensive), it can be affirmed that the basic difference is the presence de 80 kDa isoforms in the genetically hypertensive rats urine. The fact that the 80 kDa isoform do nor appear in the 1K1C and DOCA-Salt rats, whose hypertension is induced (physical factor), reinforces the hypothesis that the same is linked to a genetic factor.

Conclusion:

The results found suggest that rats, genetically predisposed to hypertension, the 80 kDa form would be detected instead of 190 kDa; this would be used to, as a consequence, as an early genetic marker for hypertension.

Segregation of the Isoform of Angiotensin I Converting Enzyme (90 kDa, N-Domain), Hypertension Genetic Marker in Rat Urine. Protocol Design to Show the Presence (Segregation of the Hypertension Genetic Marker (Protein of 90 kDa) in Rats Urine. Rats Crossing Expontaneously Hypertenses (SHR) and Brown Norway (BN).

In a previous project it was characterized the different isoforms of low molecular weight in rats urine in different experimental models (Wistar-Kyoto, SHR, 1R1C, DOCA-salt control, DOCA-salt, SHR-SP and Brown Norway). It was observed that the 90 kDa form only appears in SHR and SHR-SP rats, showing a genetic factor for the presence of such a form. In this project, it is studied the isoforms gene transmission of 190 kDa, 80 kDa and 65 kDa of the angiotensin I converting enzyme, genotype and phenotype analysis in rats urine generated from the crossings and backcrossings among SHR and Brown Norway races.

Drawing of the Crossing

Crossings were carried out between Brown Norway and SHR (BN×SHR), rats generating a group of heterozygotes rats called F1SB01 to F1SB04; from this group two animals were chosen (F1SB01 e F1SB03), males in order to carry out the backcrossing with the SHR rat (female). For phenotyping, the urine of the animals was collected and concentrated, then, it was submitted to a AcA-34 gel filtration column chromatography, together with Tris/HCl 0.05M buffer, pH 8.0, containing NaCl 0.15M. Fractions of 2.0 ml have been eluted under a 20 ml/h flux, being monitored by absorbance measured in A280 nm and by the ACE enzymatic activity using Z-Phe-His-Leu (ZPheHL) as a substrate.

Results

Parents: two peaks with ACE activity were eluted from BN rats urine and submitted to AcA-44, BN-1 e BN-2 column chromatography, with molecular weight estimated of 190 kDa and 65 kDa, respectively. On the other hand, in SHR rats urine it was found two peaks with converting activity, however, with molecular weight estimated of 90 kDa and 65 kDa, respectively.

In F1, 39 animals were generated, from which 100% were phenotyped as heterozygotes for the three, 190, 90 and 65 kDa enzyme forms. From the backcrossing animals were generated from which 85% present the three enzyme isoforms (NH group) and 15% presented the 90 and 65 kDa forms (H group).

Conclusion

Through the obtained results, it is suggested that the 90 kDa isoforms (arterial hypertension genetic marker) continue to be present in the generations originated by the crossings and backcrossings.

Expression of the Hypertension Genetic Marker, 90 kDa Isoforms in Tissues (Aorta, Adrenal, Heart, Liver, Lung, Kidney, Pancreas) of Rats Expontaneouly Hypertensives Compared With to the Wistar and Isogenic Wistar.

It as been identified in previous studies 190 and 65 kDa in Wistar, whose profile, similar to those described for normotensive individuals. 80 and 65 kDa isoforms have been identified in SHR rats urine while N-terminal ECA fragments repeats the profile, which was found for light hypertensive individuals.

The homogenates were submitted to a gel filtration chromatography and two peaks have been detected, having activity on the HHL substrate in different W and W1 rats tissue, whose molecular weights of 137 and 69 kDa are similar to those referred for W rats (Table I). The SHR rats tissues also presents two peaks of activity whose estimate molecular weights are 96 e 69 kDa, and this profile corresponded to the one found for the enzymes contained in the urine of said rats. The protein expression of the 137 and 69 kDa isoforms was observed in all tissues, which have been studied, obtained from Wistar and isogenic Wistar rats through the Western Blotting technique. By using the same technique, 96 and 69 kDa isoforms expression of all tissues of the SHR rats have been confirmed (Table I). The obtained results show the expression of the 69 kDa isoforms (besides the 137 kDa isoforms) in the W and WI tissues, as the 96 and 69 kDa isoforms in SHR rats tissues, bringing to the conclusion that the expression of N-domain isoforms, more specifically the 96 kDa isoform (hypertensive genetic marker) is not restricted only to urine and/or kidney, but are also present, locally, in the studied tissues.

TABLE I

Sumary of the study as to elution fractions and estimated molecular masses, showing the 80 kDa ECA as hypertension genetic marker.

| Strains | Enzymes | Elution Fraction (N°) | Estimated Molecular Weight (kDa) |
|---|---|---|---|
| WKY | WK-1 | 32 | 190 |
|  | WK-2 | 54 | 65 |
| SHR | S-1 | 50 | 80 |
|  | S-2 | 55 | 65 |
| 1K1C | C-1 | 32 | 140 |
|  | C-2 | 54 | 65 |
| DOCA-Salt | D-1 | 34 | 190 |
|  | D-2 | 52 | 65 |
| DOCA-Salt Control | CD-1 | 34 | 190 |
|  | CD-2 | 52 | 65 |
| SHR-SP | SP-1 | 50 | 90 |
|  | SP-2 | 55 | 65 |
| BN | BN-1 | 32 | 190 |
|  | BN-2 | 54 | 65 |
| SHR enalapril | S-1 | 50 | 80 |
|  | S-2 | 55 | 65 |
| Lyon | L-1 | 50 | 80 |
|  | L-2 | 55 | 65 |

Expression of the Hypertension Genetic Marker, 90 kDa Isoforms in the Mesangial Cells in Rats Culture, Expontaneously Hypertensesives Compared to the Wistar Rats The glomerulus has been isolated from Wistar or SHR rats, according to Greenspon and Krakomer method (1950). The rats were put under sulfuric ether atmosphere and submitted to a bilateral nefrectomy. Kidneys were decapsulated and cortical macrodissecation was carried out. The cortex was separated from the medula and then, fragments were passed through series of sieves which differ in size according to the meshes openings (60, 100 and 200 mesh). The glomerulus were collected from the surface of the third sieve and forced to pass through a (25×7) needle (aiming at to decapsulate the glomerulus. The decapsulated glomerulus were counted by using Newbauer chamber and divided (density of ~300 glomerulus/cm$^2$) in 25 cm$^2$ bottles, using RPMI 1640 supplemented with 20% of bovine fetal serum, penicillin (50 U/mL), HEPES (2.6 g) and glutamin 2 mM. The culture bottles were maintained into $CO_2$ (5%), at 37° C. Each 36 h the medium was changed. After 3 weeks approximately the primary culture of the mesangial cells were submitted to trypsin. The subcultures grew in the same medium. This procedure was repeated up to the third subcultured, when cells were prepared for the experiments: Mesangial cells (MC) (3° subcultured) were incubated for 20 hours with RPMI, without bovine fetal serum; further, the MC and the medium was collected separately.

The collected mean in the 3° subcultured was concentrated in an Amicon concentrator. The concentrated medium (2.0 mL) was submitted to a gel filtration in AcA-44 (1.5×100.8 cm column; volume 178.0 mL), equilibrated with Tris-HCl 50 mM buffer, pH 8.0, containing NaCl 150 mM. Fractions of 2.0 mL under flux of 20 mL/h were collected. Elution was carried out under a 20 mL flux by one hour. Fractions of 2 mL were collected, and monitored by absorbance measurements in 280 nm and the enzymatic activity was quantified, by using Hippuryl-His-Leu (HHL).

The CM collected were lysed with 4 mL Tris-HCl 50 mM buffer, pH 8.0, containing Triton X-114 1% and PMFS 0.5 mM, through mechanical agitation, by one hour, at 4° C. After this period, the lysed cells were centrifuged and the supernatant was collected and concentrated an Amicon concentrator, under nitrogen pressure, at 3 kgf/cm$^2$. Further, 2mL was submitted to a gel filtration chromatography.

The results obtained for MC in Wistar and SHR rats culture presented the same chromatographic profile obtained for human urine of normal individuals and moderated hypertension patients as well as for urine of Wistar and SHR rats, thus, confirming that in kidneys, more specifically in the glomerulus, the different isoforms, already mentioned are produced (Table II).

TABLE II

Summary of the study groups as to determinate molecular masses.

| Tissues | Wistar | Wistar Isogenic | SHR |
|---|---|---|---|
| Adrenal | 137 | 137 | 96 |
|  | 69 | 69 | 69 |
| Aorta | 137 | 137 | 96 |
|  | 69 | 69 | 69 |
| Heart | 137 | 137 | 96 |
|  | 69 | 69 | 69 |
| Liver | 137 | 137 | 96 |
|  | 69 | 69 | 69 |
| Lung | 137 | 137 | 96 |
|  | 69 | 69 | 69 |

TABLE II-continued

Summary of the study groups as to determinate molecular masses.

| Tissues | Wistar | Wistar Isogenic | SHR |
|---|---|---|---|
| Kidney | 137 | 137 | 96 |
|  | 69 | 69 | 69 |
| Testicle | 137 | 137 | 96 |
|  | 69 | 69 | 69 |

Final Conclusion:

Based on the fact that 90 kDa ACE only appears in hypertensive patients/MC of SHR/urine of SHR rats, it is suggested that it could have an important and specific role as a hypertension genetic marker.

Based on the studies obtained with the parents and children there was observed that 190, 90 e 65 kDa isoforms are present in normal individuals from hypertensive parents showing that a segregation of this isoform, thus, it could be characterized as a hypertensive predictor. These data were confirmed in crossing and backcrossing of Brown Norway and SHR rats (Table III).

TABLE III

ECA isoforms detected in the extracellular and lysed cells mesangial cells in Wistar and SHR rats culture.

| Rats | Extracelular | Intracelular |
|---|---|---|
| Wistar | 130 kDa | 135 kDa |
|  | 60 kDa | 68 kDa |
| SHR | 80 kDa | 80 kDa |
|  | 60 kDa | 68 kDa |

REFERENCES

LANZILLO J J, FANBURG B L. Low molecular weight angiotensin I-converting enzyme from rat lung. *Biochem Biophys Acta* 491: 339-344, 1977.

NISHIMURA K, YOSHIDA N, HIWADA K, UEDA E, KOKUBU T. Properties of three different forms of angiotensin I-converting enzyme from human lung. *Biochem Biophys Acta* 522: 229-237, 1978.

NAGAMATSU A, INOKUCHI J I, SOIDA S. Two different forms of angiotensin I-converting enzyme from hog kidney. *Chem. Pharm. Bull.* 28: 459-464, 1980.

TAKADA Y, HIWATA K, KOKUBU T. Isolation and characterization of angiotensin converting enzyme from human kidney. *J Biochem* 90: 1309-1319, 1981

IWATA K, BLACHER R, SOFFER R L, LAI CHUNLAW. Rabbit pulmonary angiotensin-converting enzyme: the NH2-terminal fragment with enzymatic activity and its formation from the native enzyme by $NH_4OH$ treatment. *Arch Biochem Biophys* 227: 188-201, 1983.

YOTSUMOTO H, LANZILLO J J, FANBURG B L. Generation of a 90000 molecular weight fragment from human plasma angiotensin I-converting enzyme by enzymatic or alkaline hydrolysis. *Biochem Biophys Acta* 749: 180-184, 1983.

LANTZ I, NYBERG F, TERENIUS L. Molecular heterogeneity of angiotensin converting enzyme in human cerebrospinal fluid. *Biochem Int* 23: 941-948, 1991.

DEDDISH P A, WANG J, MICHEL B, MORRIS P W, DAVIDSON N O, SKIDGEL R A, ERDOS E G. Naturally occurring active N-domain of human angiotensin I-converting enzyme. *Proc Natl Acad Sci USA* 91: 7807-7811, 1994.

RYAN J W, OZA N B, MARTIN L C, PENA G A. Biochemistry, Pathophysiology and Clinical aspects. Components of the kallikrein-kinin system in urine, in *Kinin II* (vol 10), edited by Fuji S, Moryia H, Suzuki T, Plenun Press, New York, 1978, pp 313-323.

KOKUBU T, KATO I, NISHIMURA K, HIWADA K, UEDA E. Angiotensin I-converting enzyme in urine. *Clin Chim Acta* 89: 375-379,1978.

SKIDGEL R A, WEARE J A, ERDÖS E G. Purification and characterization of human converting enzyme (kininase II). *Peptides* 2: 145-152, 1987

CASARINI D E. Purificação e caracterização de duas peptidases com atividade cininásica encontradas em urina humana. Dissertação de Mestrado apresentada à Universidade Federal de São Paulo, Escola Paulista de Medicina, 1983.

CASARINI D E, RIBEIRO E B, SCHOR N, SIGULEM D. Study of angiotensin I converting enzyme in isolated and artificially perfused kidney. Arq. Biol. Tecnol. 30 (1): 58, 1987.

CASARINI D E, ALVES K B, COSTA R H, PLAVINIC F L, MOREIRA MEM, RODRIGUES CIS, MARSON O. (1991). Effect of diuretic upon urinary levels of angiotensin converting enzyme (ACE) of essencial mild hypertensive patients (EPH). Hypertension 17 (3): 463.

CASARINI D E, ALVES K B, ARAUJO M S, STELLA R C R. Endopeptidase and carboxipeptidase activities in human urine which hydrolyze bradykinin. *Braz J Med Biol Res* 25: 219-229, 1992.

CASARINI D E, CARMONA A K, PLAVINIK F L, JULIANO L, ZANELLA M T, RIBEIRO A B. Effects of Ca2+ channel blockers as inhibitors of angiotensin I-converting enzyme. Hypertension 26 (6), parte II, 1145-1148, 1995.

CASARINI D E, PLAVINIK F L, ZANELLA M T, MARSON O, KRIEGER J E, HIRATA I Y, STELLA R C R. Angiotensin converting enzymes from humanurine of mild hypertensive patients resemble the N-terminal fragment of human angiotensin converting enzymes. International Journal of Biochemistry and Cell Biology 33:75-85, 2001.

ALVES K B, CASARINI D E, COSTA R H, PLAVINIC F L, PORTELA J E and MARSON O. Angiotensin converting enzymes (ACE) from urine of treated and untreated essential mild hipertensive patients (EHP) with diuretic: partial purification and characterization. Agents and Actions 38/III: 270-277, 1992. COSTA R H, CASARINI D E, PORTELA J E, PLAVINIK F L, ALVES K B, MARSON O Enzimas conversoras de angiotensina en orina de hipertensos renovasculares, no tratados con diureticos: purification y caracterization. Revista Espanhola de Nefrologia 23(S5): 14-17, 1993.

COSTA R H, CASARINI D E, PLAVNIK F L, MARSON O, ALVES K B. Angiotensin converting I-enzymes from urine of untreated renovascular hypertensive and normal patients: purification and characterization Immunopharmacology 46: 237-246, 2000.

BAGGIO B, FAVARO S, CANTARO S, BERTAZZO L, FUNZIO A, BORSATTI A. Increased urinary angiotensin converting enzyme in patients with upper tract infection. *Clin Chim Acta* 109: 211-218, 1981.

KATO I, TAKATA K, NISHIMURA K, HIWADA K, KOKUBU T. Increased urinary excretion of angiotensin converting enzyme in patients with renal diseases. *J Clin Chem Clin Biochem* 20: 473-476, 1982.

ANDRADE M C C, QUINTO B M R., CARMONA A K, RIBAS O S, BOIM M A, SCHOR N, CASARINI D E. Purification and characterization of angiotensin I-converting enzymes from mesangial cells in culture. Journal of Hypertension 16: 2063-2074, 1998.

HATTORI M A, DEL BEM G, CARMONA A K, CASARINI D E. Angiotensin converting enzymes (hight and low molecular weight) in urine of premature and full term infants. Hypertension 35: 1284-1290, 2000.

The invention claimed is:

1. A method of detecting a predisposition for the development of hypertension in an individual, comprising detecting a presence of the following three angiotensin converting enzyme isoforms in an aliquot of fresh or concentrated biological fluids, cells or tissues obtained from the individual, wherein the three angiotensin converting enzyme isoforms are 65 kDa, 90 kDa, and 190 kDa, and wherein the 65 kDa and 190 kDa isoforms are present in a normotensive patient, and wherein the 65 kDa, 90 kDa, and 190 kDa isoforms must be present to indicate the predisposition for the development of hypertension.

2. The method of claim 1, wherein the aliquot of fresh or concentrated biological fluids, cells or tissues is urine.

3. The method of claim 1, wherein said detecting step comprises an immunoprecipitation method.

4. The method of claim 3, wherein the immunoprecipitation method is Western blotting.

5. The method of claim 1, wherein said detecting step comprises a mass detection methodology.

6. The method of claim 5, wherein the mass detection methodology comprises mass spectroscopy.

7. The method of claim 5, wherein the mass detection methodology is used in combination with a chromatographic separation.

8. The method of claim 7, wherein the mass detection methodology comprises mass spectroscopy.

9. The method of claim 5, wherein the mass detection spectroscopy is high performance liquid chromatography in combination with mass spectrometry (HPLC-MS).

* * * * *